(12) United States Patent
Sim et al.

(10) Patent No.: US 9,572,929 B2
(45) Date of Patent: Feb. 21, 2017

(54) BLOOD COLLECTION ASSEMBLY HAVING A MULTI-FUNCTION SHIELD

(71) Applicant: Becton, Dickinson and Company, Franklin Lakes, NJ (US)

(72) Inventors: Lee Hoong Sim, Singapore (SG); Tiong Yee Sim, Kukai Johor (MY)

(73) Assignee: Becton, Dickinson and Company, Franklin Lakes, NJ (US)

( * ) Notice: Subject to any disclaimer, the term of this patent is extended or adjusted under 35 U.S.C. 154(b) by 21 days.

(21) Appl. No.: 13/788,277

(22) Filed: Mar. 7, 2013

(65) Prior Publication Data

US 2013/0237927 A1 Sep. 12, 2013

Related U.S. Application Data

(60) Provisional application No. 61/608,195, filed on Mar. 8, 2012.

(51) Int. Cl.
*A61M 5/158* (2006.01)
*A61B 5/15* (2006.01)
(Continued)

(52) U.S. Cl.
CPC .......... *A61M 5/158* (2013.01); *A61B 5/15003* (2013.01); *A61B 5/1545* (2013.01);
(Continued)

(58) Field of Classification Search
CPC ............ A61M 5/3216; A61M 2005/3217; A61M 25/0631; A61M 5/3219; A61M 5/321; A61M 5/158; A61B 5/1438; A61B 5/15003; A61B 5/150267; A61B 5/150389; A61B 5/150496; A61B 5/150618; A61B 5/150633; A61B 5/150664; A61B 5/150656; A61B 5/155; A61B 5/150717; A61B 5/150732; A61B 5/1545; A61B 5/150488; A61B 5/150587
(Continued)

(56) References Cited

U.S. PATENT DOCUMENTS 4,944,397 A * 7/1990 Miller ........................ 206/365
5,405,332 A * 4/1995 Opalek ........................ 604/192
(Continued)

FOREIGN PATENT DOCUMENTS

| EP | 1346739 A1 | 9/2003 |
|---|---|---|
| WO | 98/11928 A1 | 3/1998 |
| WO | 2008/109845 A2 | 9/2008 |

OTHER PUBLICATIONS

American Heritage Dictionary Definition for "Unitary". Checked Dec. 11, 2015 and available online at https://www.ahdictionary.com/word/search.html?q=unitary.*

*Primary Examiner* — Theodore Stigell
*Assistant Examiner* — Amber Stiles
(74) *Attorney, Agent, or Firm* — The Webb Law Firm

(57) ABSTRACT

A needle assembly includes a housing having proximal and distal ends, an IV cannula projecting distally from the housing, and an IV shield having an engagement. The housing has a shield seat and the IV cannula has a distal tip. The IV shield has a pre-use position where the IV shield covers the distal tip of the IV cannula and the engagement is disengaged from the shield seat, and a use position where the engagement is engaged with the shield seat and the IV shield is adapted to move between a non-shielded position, in which the distal tip is exposed, and a shielded position, in which the distal tip is shielded by the IV shield.

23 Claims, 20 Drawing Sheets

(51) Int. Cl.
*A61B 5/154* (2006.01)
*A61M 5/32* (2006.01)
*A61B 5/155* (2006.01)

(52) U.S. Cl.
CPC .. *A61B 5/150267* (2013.01); *A61B 5/150389* (2013.01); *A61B 5/150488* (2013.01); *A61B 5/150496* (2013.01); *A61B 5/150572* (2013.01); *A61B 5/150587* (2013.01); *A61B 5/150595* (2013.01); *A61B 5/150618* (2013.01); *A61B 5/150633* (2013.01); *A61B 5/150656* (2013.01); *A61B 5/150664* (2013.01); *A61B 5/150717* (2013.01); *A61B 5/150732* (2013.01); *A61B 5/155* (2013.01); *A61M 5/3216* (2013.01)

(58) Field of Classification Search
USPC ......... 604/128, 149, 192–198, 263, 411–415
See application file for complete search history.

(56) References Cited

U.S. PATENT DOCUMENTS

| | | | |
|---|---|---|---|
| 5,509,907 A | * | 4/1996 | Bevilacqua ......... A61M 5/3216 604/192 |
| 5,662,617 A | | 9/1997 | Odell et al. |
| 2003/0181860 A1 | * | 9/2003 | Swenson ........................ 604/192 |
| 2003/0220614 A1 | | 11/2003 | Crawford |
| 2003/0229315 A1 | | 12/2003 | Leong et al. |
| 2005/0148942 A1 | * | 7/2005 | Newby ................. A61M 5/002 604/192 |
| 2008/0306451 A1 | * | 12/2008 | Woehr ................ A61M 5/3216 604/198 |
| 2011/0178427 A1 | | 7/2011 | Tan et al. |
| 2011/0288496 A1 | * | 11/2011 | Harms ................ A61M 5/3216 604/263 |

\* cited by examiner

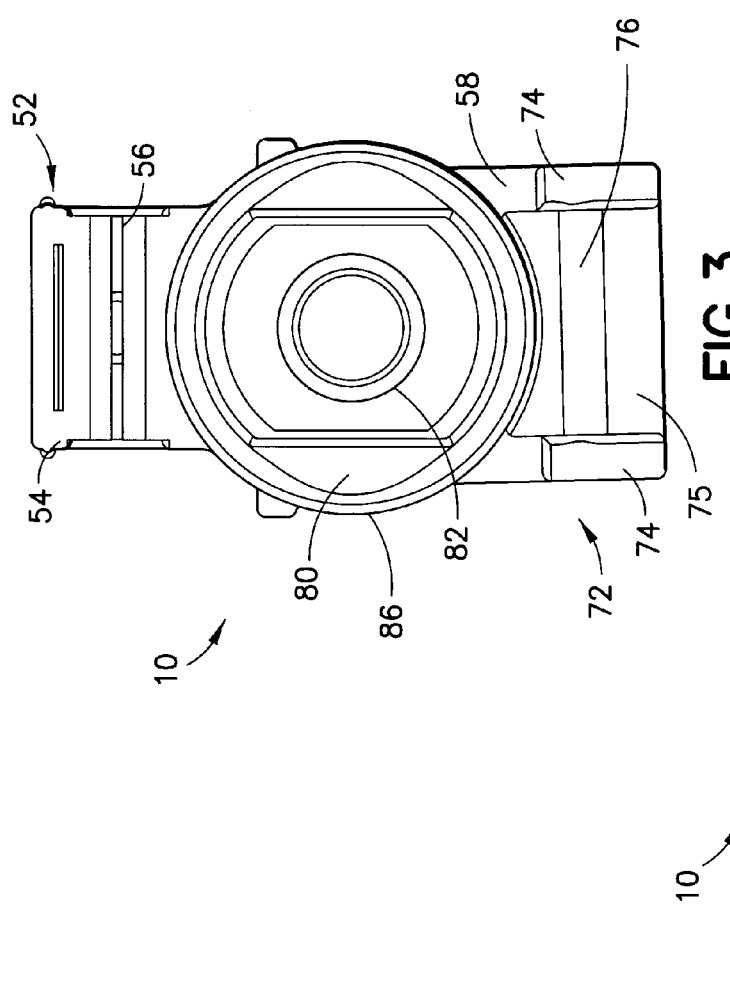
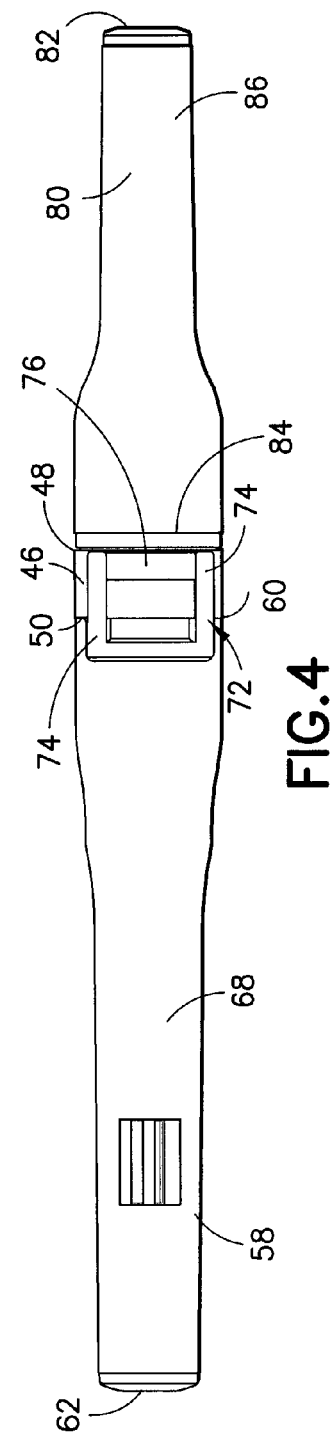
FIG. 3
FIG. 4

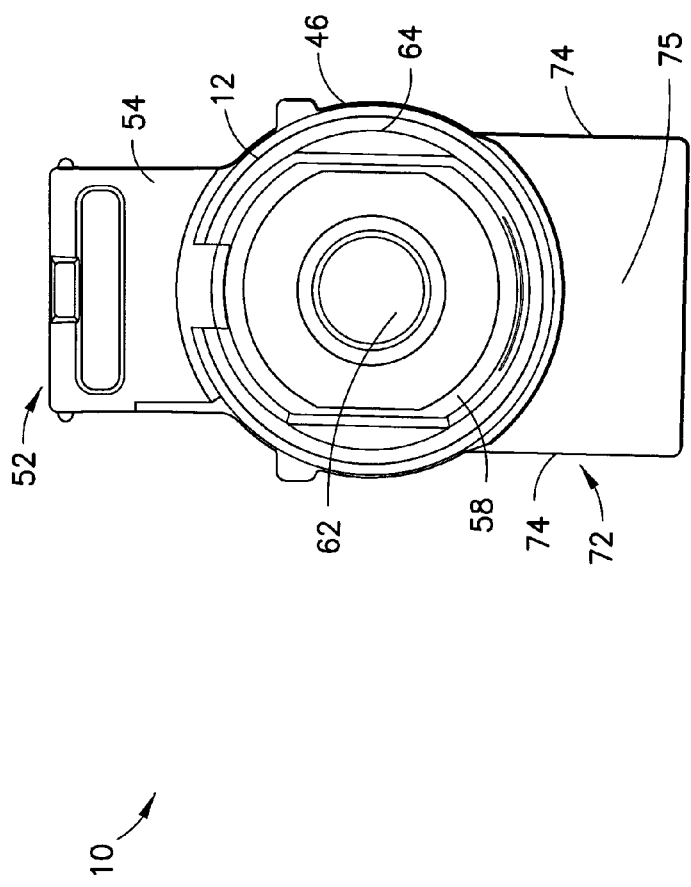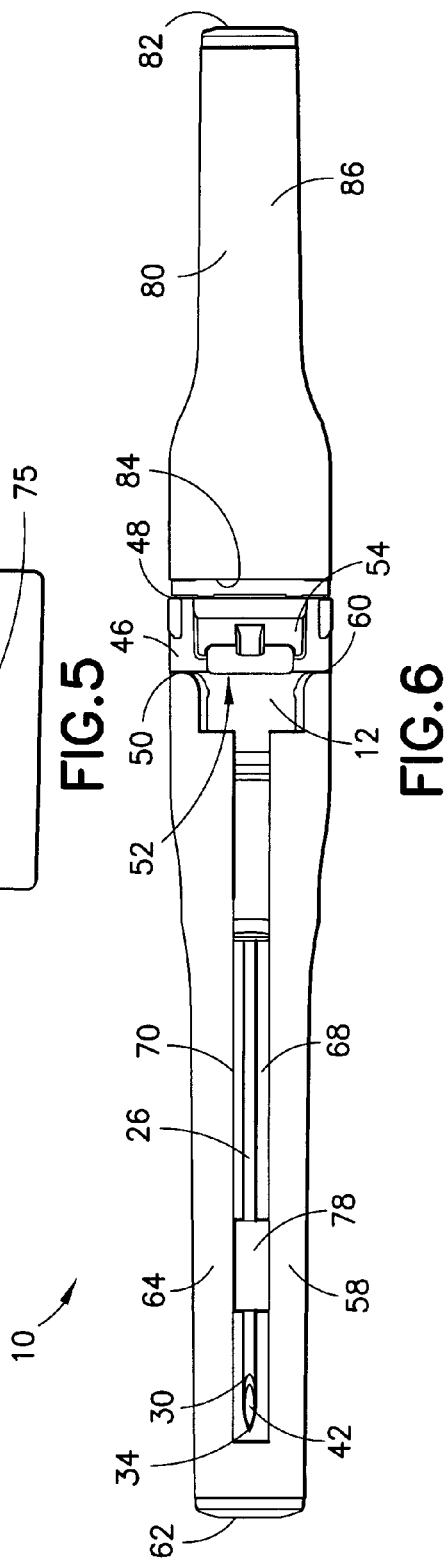

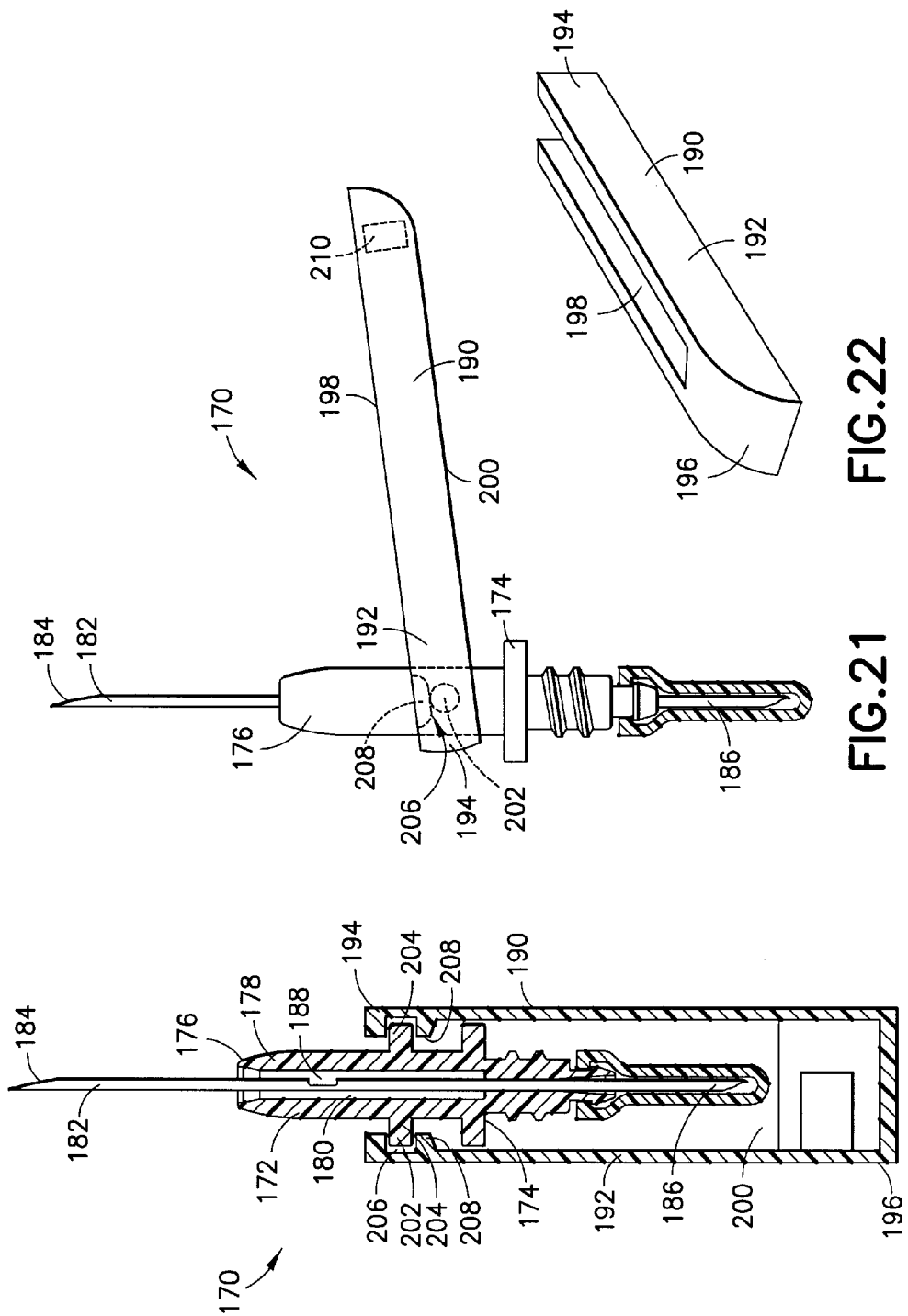

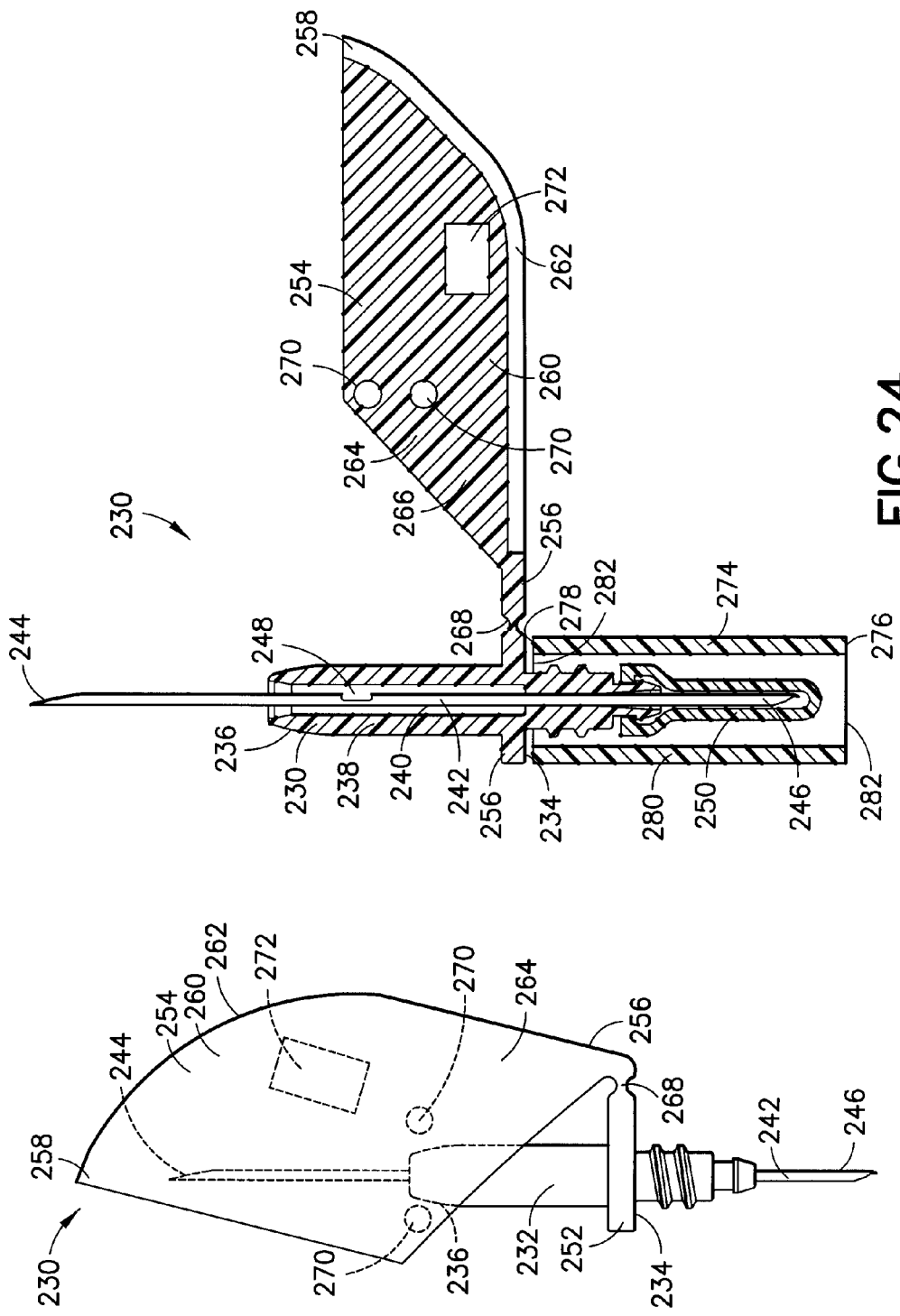

BLOOD COLLECTION ASSEMBLY HAVING A MULTI-FUNCTION SHIELD

CROSS-REFERENCE TO RELATED APPLICATION

The present application claims priority to U.S. Provisional Application No. 61/608,195, filed Mar. 8, 2012, entitled "Multi-Functions Shield for Blood Collection", the entire disclosure of which is hereby incorporated by reference.

BACKGROUND OF THE INVENTION

Field of the Invention

The present invention relates to a needle assembly and, more particularly, to a shieldable blood collection needle assembly.

Description of Related Art

Needle assemblies are used for collecting specimens of fluid, such as blood, from a patient. Some such needle assemblies are intended for use with an evacuated tube and include a housing with a proximal end, a distal end, and a passage extending between the ends. Such needle assemblies further include at least one needle cannula mounted to the housing. The needle cannula includes a sharply pointed distal end that projects distally beyond the housing, a proximal end that projects proximally beyond the housing, and a lumen that provides communication between the opposed ends of the needle cannula. Some needle assemblies include separate proximal and distal cannulas and rely upon a portion of the housing to provide communication between the lumens of the respective cannulas. The distal end of the needle cannula typically is beveled to a tip that is sufficiently sharp for piercing the skin of the patient and accessing the vein or other source of fluid that is to be collected. The proximal end of the needle cannula is configured for piercing the rubber stopper on an evacuated tube. The proximal end of the needle cannula typically is covered by a needle pierceable resealable multi-sample sleeve. The sleeve is compressed by the rubber stopper of the evacuated tube and punctured by the proximal end of the needle cannula as the proximal end of the needle cannula is urged into communication with the evacuated tube. The evacuated tube is typically received by a needle holder secured to the proximal end of the housing.

Prior to use, the needle assembly also typically includes an IV shield and a non-patient shield mounted respectively over the distal end of the needle cannula and the proximal end of the needle cannula. The IV shield and the non-patient shield are frictionally retained on the housing and can be separated through axial movement of the shields away from the housing. The combined needle assembly and evacuated tube is employed by initially urging the pointed distal end of the needle cannula into a blood vessel of a patient. Once the targeted blood vessel has been accessed, the evacuated tube is urged into the needle holder such that the proximal point of the needle cannula pierces the septum of the tube. Low pressure conditions within the evacuated tube, as well as the patient's own vasculature pressure, generate a flow of blood from the patient through the needle cannula and into the evacuated tube. The evacuated tube may be removed from the needle holder after a sufficient quantity of blood has been collected. One or more additional evacuated tubes may similarly be urged into the open end of the needle holder for drawing one or more additional samples of blood to be analyzed. The needle cannula is then withdrawn from the patient after a sufficient volume of blood has been collected for the required analytical procedure.

Many fluid collection needle assemblies are provided with a flashback chamber that communicates with the needle cannula. The flashback chamber typically is formed at least partly from a transparent or translucent material and is intended to receive a portion of the blood flow shortly after a vein has been accessed properly. The flashback chamber gives a positive indication of venous entry after a vein is entered with the distal end of the needle cannula.

In order to reduce the risk of an accidental needle stick, or contact that could transmit pathogens from the patient to the medical practitioner, the needle cannula is shielded after contact with the patient. Shields have taken many different forms. For example, some shields telescope over the needle cannula and frictionally engage the housing. Other shields are telescoped over the housing and can be moved distally over the needle cannula to effect shielding. Other shields are hingedly mounted to or near the housing and can be rotated from an open position, where the needle cannula is exposed, to a closed position, where the needle cannula is shielded.

SUMMARY OF THE INVENTION

In one embodiment, a needle assembly includes a housing having proximal and distal ends, an IV cannula projecting distally from the housing, and an IV shield having an engagement. The housing has a shield seat and the IV cannula has a distal tip. The IV shield has a pre-use position where the IV shield covers the distal tip of the IV cannula and the engagement is disengaged from the shield seat, and a use position where the engagement is engaged with the shield seat and the IV shield is adapted to move between a non-shielded position, in which the distal tip is exposed, and a shielded position, in which the distal tip is shielded by the IV shield.

The IV shield may include a body that defines a longitudinal slot adapted to receive the IV cannula and a needle catch adapted to engage the IV cannula when the IV shield is in the shielded position. The body of the IV shield may engage the distal end of the housing when the IV shield is in the pre-use position and the IV shield may be pivotable relative to the housing when the IV shield is in the use position. The engagement may comprise a locking pin and the IV shield may be pivotable about the locking pin in the use position. The needle assembly may further include a non-patient cannula projecting from the housing, and a non-patient shield for removably shielding the non-patient cannula adapted to engage the proximal end of the housing. The shield seat may include a projection that defines an opening to receive the engagement of the IV shield. The opening of the shield seat may be tapered to lock the engagement to the shield seat after insertion of the engagement into the opening. The engagement may comprise a locking pin with the shield seat substantially c-shaped about the locking pin.

In a further embodiment, a needle assembly includes a housing having proximal and distal ends and a shield seat, a cannula having an IV end projecting distally from the housing and a non-patient end projecting proximally from the housing, and a shield secured to the housing. The shield has a pre-use position where the shield covers the non-patient end of the cannula, and a use position where the shield is capable of covering the IV end of the cannula.

The housing may have a chamber wall extending between the proximal and distal ends for defining a chamber in the housing. The cannula may define an opening in fluid communication with the chamber. The housing may have a first portion and a second portion with the first portion secured to the second portion, and where the shield and the first portion of the housing are formed integrally. The shield may be secured to the first portion of the housing via a living hinge, and the shield may be pivotable between a non-shielded position and a shielded position. The shield may include a non-patient portion adapted to cover a portion of the non-patient end of the cannula and an IV portion adapted to cover a portion of the IV end of the cannula. The IV portion of the shield may include a needle catch adapted to engage the IV end of the cannula when the shield is in the use position. The shield may include a non-patient portion adapted to cover a portion of the non-patient end of the cannula, and an IV portion adapted to cover a portion of the IV end of the cannula, where the IV portion of the shield includes a needle catch adapted to engage the IV end of the cannula when the shield is in the use position. The housing may include a projection with the shield secured to the housing about the projection and with the shield being pivotable relative to the housing between the pre-use position and the use position. The cannula may include two distinct cannulae. The shield may be engaged with the shield seat in the use position and capable of rotating from a non-shielded position, in which a tip of the IV end is exposed, to a shielded position, in which the tip of the IV end is shielded.

In another embodiment, a needle assembly includes a housing having proximal and distal ends, a cannula having an IV end projecting distally from the housing and a non-patient end projecting proximally from the housing, and an IV shield pivotally secured to the housing. The IV shield has a pre-use position, where the IV shield covers a portion of the IV end of the cannula, and a use position, where the IV shield is adapted to move between a non-shielded position and a shielded position. At least one of the sidewalls includes a first projection adapted to temporarily engage the housing when the IV shield is in the pre-use position, and at least one of the sidewalls includes a second projection adapted to permanently engage the housing when the IV shield is in the shielded position.

In certain configurations, the sidewalls are spaced via an end wall extending between the pair of sidewalls. In other configurations, the IV shield includes a needle catch adapted to engage the IV end of the cannula when the IV shield is in the shielded position. Each of the sidewalls may include a pair of semi-spherical projections adapted to temporarily engage the housing when the IV shield is in the pre-use position.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

FIG. 3 is a right side view of the needle assembly of FIG. 1 in accordance with an embodiment of the present invention.

FIG. 4 is a top view of the needle assembly of FIG. 1 in accordance with an embodiment of the present invention.

FIG. 5 is a left side view of the needle assembly of FIG. 1 in accordance with an embodiment of the present invention.

FIG. 6 is a bottom view of the needle assembly of FIG. 1 in accordance with an embodiment of the present invention.

FIG. 20 is a cross-sectional view of a needle assembly according to an embodiment of the present invention.

FIG. 21 is a front view of the needle assembly of FIG. 20 showing a shield in a non-shielded position in accordance with an embodiment of the present invention.

FIG. 22 is a perspective view of the shield shown in FIG. 20 in accordance with an embodiment of the present invention.

FIG. 23 is a front view of a needle assembly showing a shield in a pre-use position according to an embodiment of the present invention.

FIG. 24 is a partial cross-sectional view of the needle assembly of FIG. 23 showing the shield in a use position and in a non-shielded position in accordance with an embodiment of the present invention.

DESCRIPTION OF PREFERRED EMBODIMENTS

Figure 1:
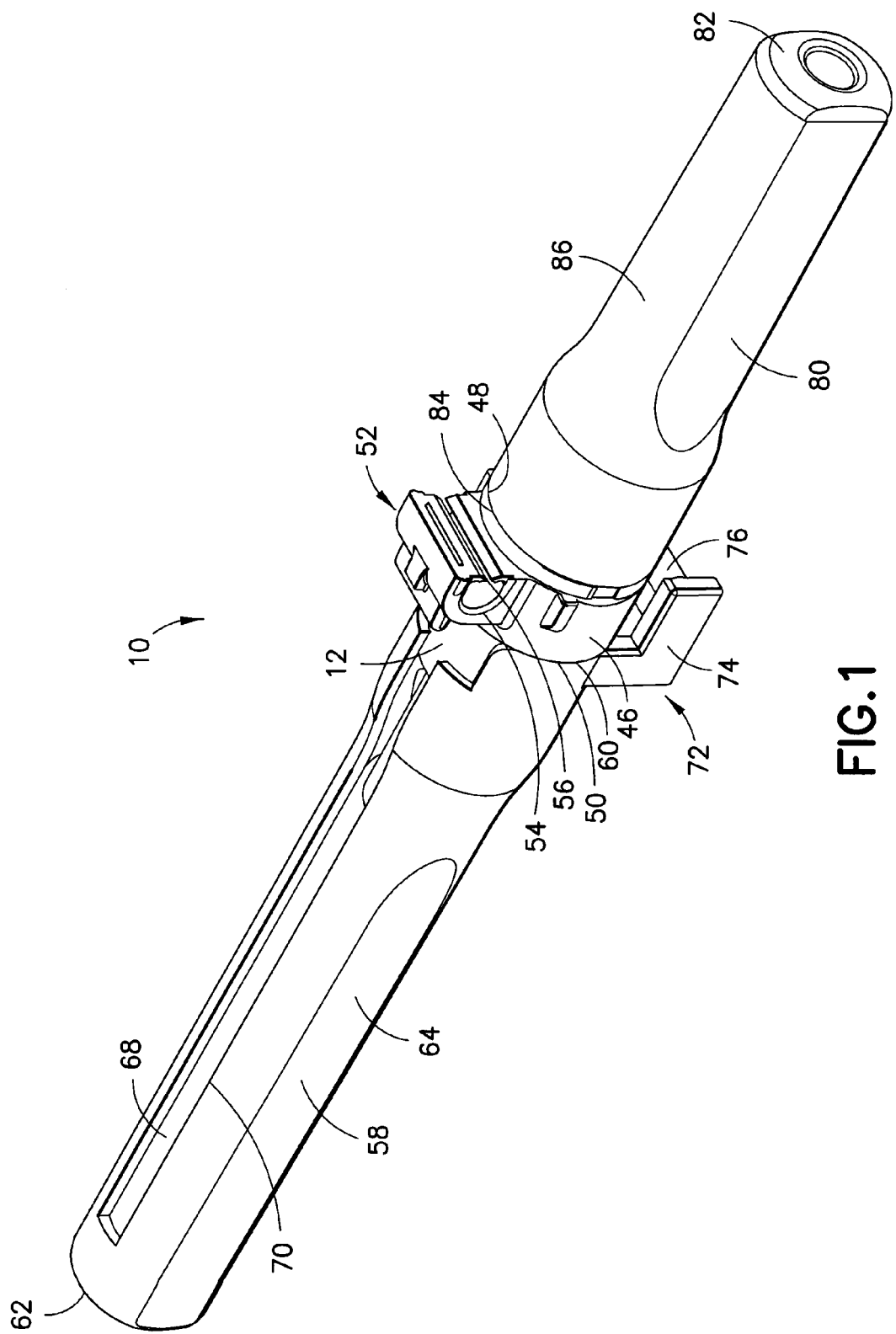
FIG. 1 is a perspective view of a needle assembly according to an embodiment of the present invention.
Figure 2:
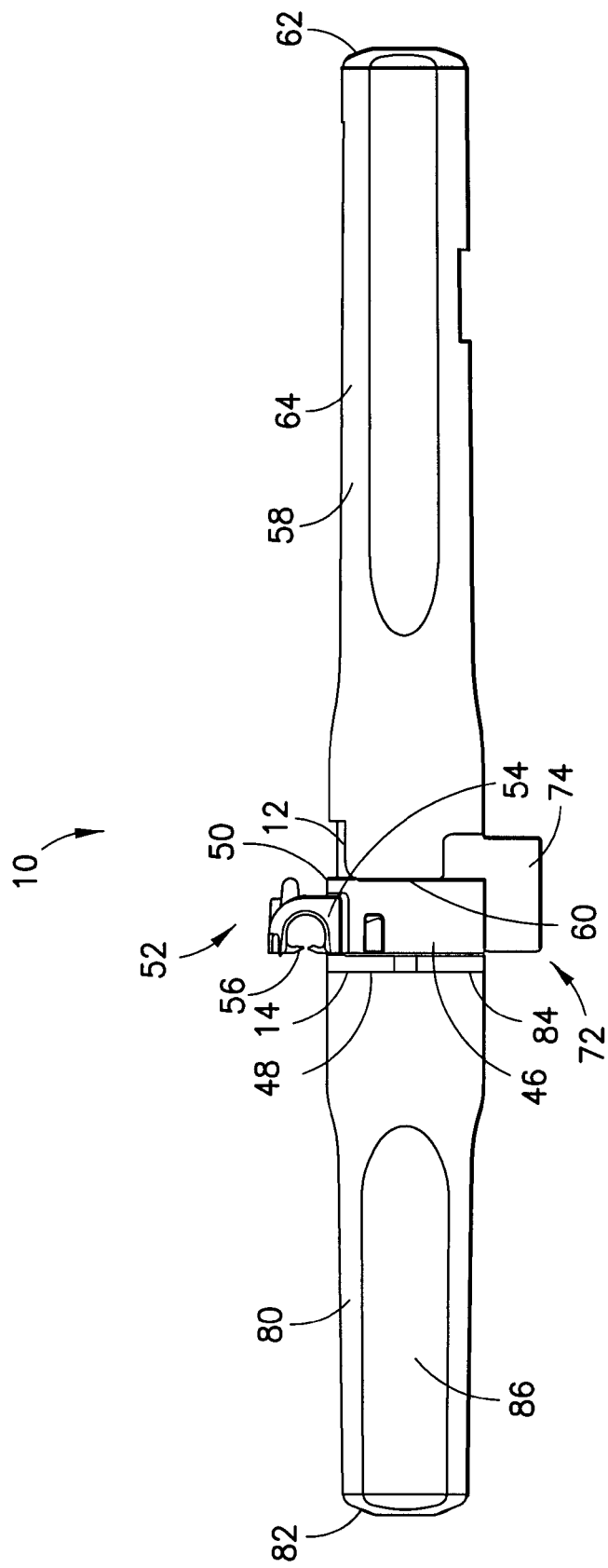
FIG. 2 is a front view of the needle assembly of FIG. 1 in accordance with an embodiment of the present invention.
Figure 7:
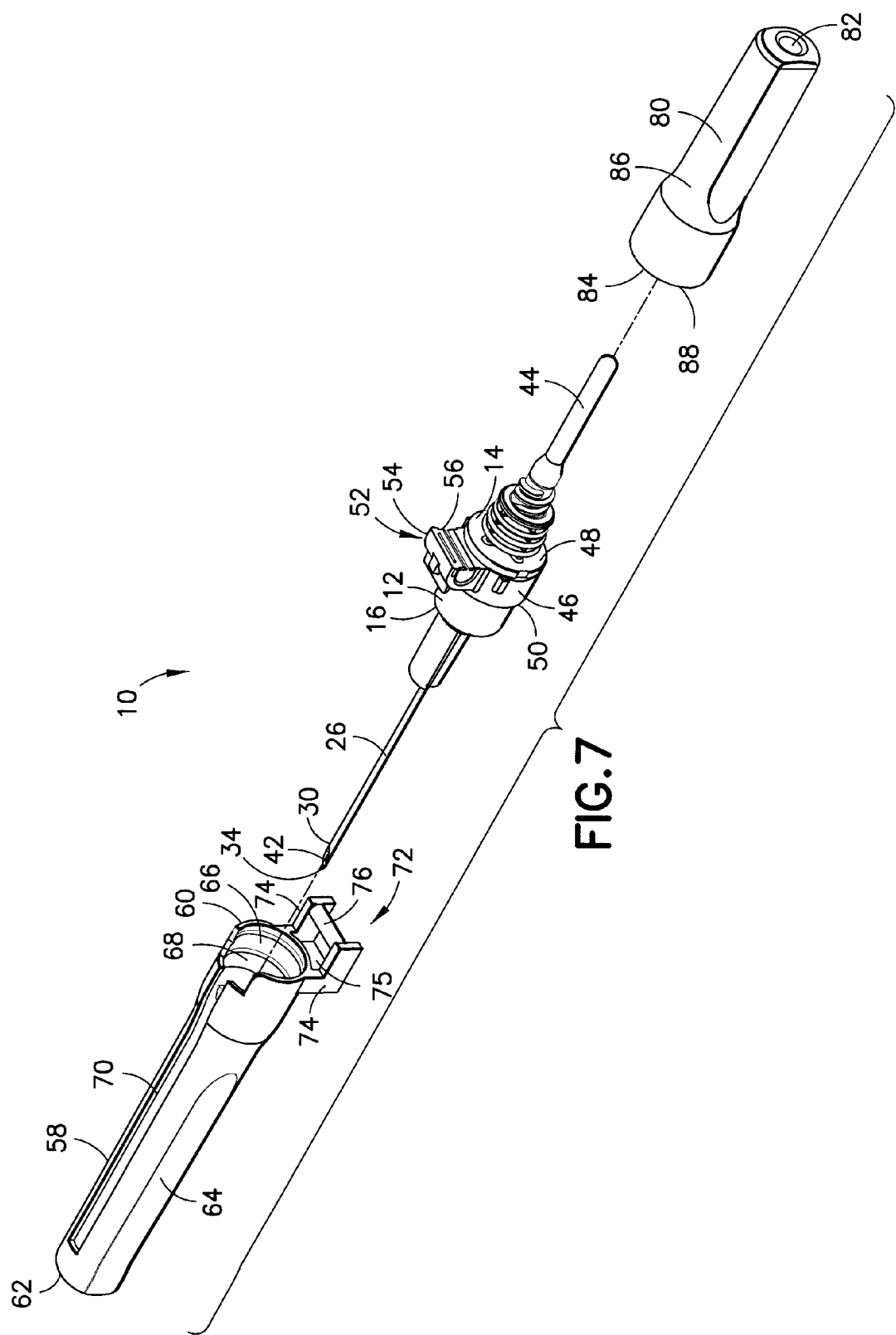
FIG. 7 is an exploded perspective view of the needle assembly of FIG. 1 in accordance with an embodiment of the present invention.
Figure 8:
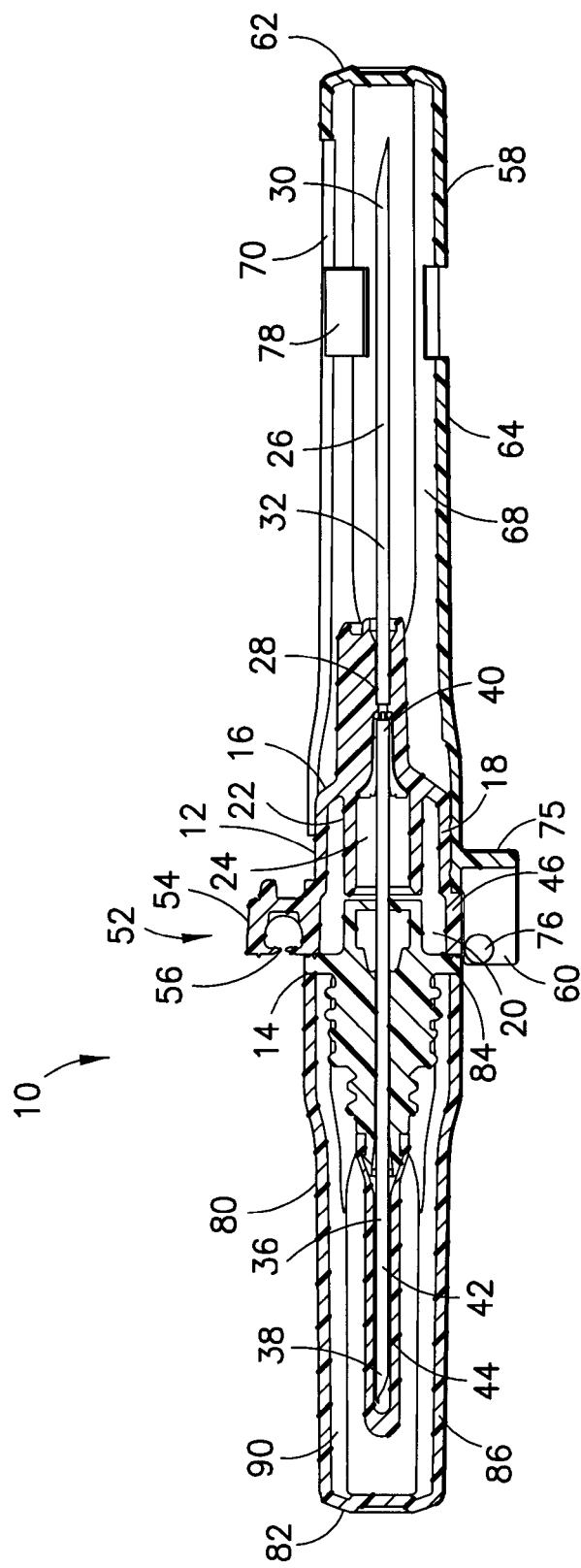
FIG. 8 is cross-sectional view of the needle assembly of FIG. 1 in accordance with an embodiment of the present invention.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Referring to FIGS. 1-18, one embodiment of a needle assembly 10 includes a housing 12 with a proximal end 14, a distal end 16, and a generally cylindrical-shaped outer sidewall 18 extending between the ends 14, 16. Outer sidewall 18 is formed from a transparent or translucent plastic material and defines a chamber 20 within the housing between the proximal and distal ends 14, 16. The housing 12 also includes a generally cylindrical-shaped inner sidewall 22 that extends from the distal end 16 toward the proximal end 14. The inner sidewall 22 is substantially concentrically disposed within the outer sidewall 18 and is also formed from a transparent or translucent plastic material. The inner sidewall 22 defines a flashback chamber 24 such that fluid collected in the flashback chamber 24 can be observed from locations externally of the needle assembly 10. The flashback chamber 24 is in fluid communication with the chamber 20 such that the chamber 20 may also contribute to an indication of flashback.

The needle assembly 10 further includes an IV cannula 26 with a proximal end 28, a distal end 30, and a lumen 32 extending between the ends 28, 30. The distal end 30 of the IV cannula 26 is disposed externally of the housing 12 and includes a distal tip 34 that is beveled to a sufficiently sharp tip for piercing skin and tissue of a patient. The IV cannula 26 is secured to the housing 12 with the proximal end 28 of the IV cannula 26 positioned substantially adjacent to the distal end 16 of the housing 12. The lumen 32 of the IV cannula 26 is in fluid communication with the flashback chamber 24. The needle assembly 10 also includes a non-patient cannula 36 secured to the proximal end 14 of the housing 12. The non-patient cannula 36 includes a proximal end 38 disposed externally of the housing 12, a distal end 40 disposed adjacent to the flashback chamber 24, and a lumen 42 extending between the ends 38, 40. The proximal end 38 is adapted to pierce a rubber stopper of an evacuated tube, which is discussed in more detail below. The lumen 42 of the non-patient cannula 36 is substantially axially aligned with the lumen 32 of the IV cannula 26. A sleeve 44 is mounted over a portion of the non-patient cannula 36 that is disposed externally of the housing 12. The sleeve 44 is mounted to the proximal end 14 of the housing 12 and is formed from a material that is substantially impervious to liquid, readily pierceable by the proximal end 38 of the non-patient cannula 36, and resiliently resealable. The sleeve 44 is adapted to collapse distally upon being engaged by the rubber stopper of an evacuated tube. The IV cannula 26, the non-patient cannula 36, and the housing 12 cooperate to provide an early indication of venous entry due to the flashback of blood in the flashback chamber 24 and/or the chamber 20 of the housing 12. Other suitable flashback arrangements, however, may be utilized such as arrangements using vented plugs.

Referring still to FIGS. 1-18, the needle assembly 10 includes a collar 46 that extends circumferentially around the housing 12 at the proximal end 14 thereof. The collar 46 is formed integrally with the housing 12, but also may be formed separately and mechanically secured to the housing 12. The collar 46 has a proximal end 48 axially spaced from a distal end 50. The collar 46 is provided with a shield seat 52 that includes a C-shaped projection 54 extending radially outward from the collar 46 and defining a tapered opening 56.

The needle assembly 10 further includes an IV shield 58 with a proximal end 60 and a distal end 62. The IV shield 58 includes an elongate body 64 that defines an opening 66 adjacent to the proximal end 60 of the IV shield 58 and an interior space 68 that is adapted to receive the IV cannula 26. The elongate body 64 also defines a longitudinal slot 70 that extends from the proximal end 60 to a position adjacent to the distal end 62 of the IV shield 58. In particular, the longitudinal slot 70 extends from the opening 66 of the elongate body 64 in a direction extending along a longitudinal axis of the elongate body 64 toward the proximal end 60 of the IV shield 58. Further, the elongate body 64 of the IV shield 58 includes an engagement 72 that is adapted to be secured to the shield seat 52 of the housing 12. The engagement 72 includes a pair of L-shaped extensions 74 extending from the elongate body 64 of the IV shield 58 with a back plate 75 extending between the L-shaped extensions 74. A pin 76 extends laterally between the L-shaped extensions 74. The pin 76 is shaped and configured to be received by the tapered opening 56 of the shield seat 52, which is discussed in more detail below. The pin 76 is cylindrically-shaped, although other suitably shaped pins may be utilized. The IV shield 58 also includes a needle catch 78 positioned within the interior space 68 that is adapted to be secured and locked to the IV cannula 26. The needle assembly 10 also includes a non-patient shield 80 with a proximal end 82 and a distal end 84. The non-patient shield 80 includes an elongate body 86 that defines an opening 88 adjacent to the proximal end 82 of the non-patient shield 80 and an interior space 90 that is adapted to receive the non-patient cannula 36.

Figure 9:
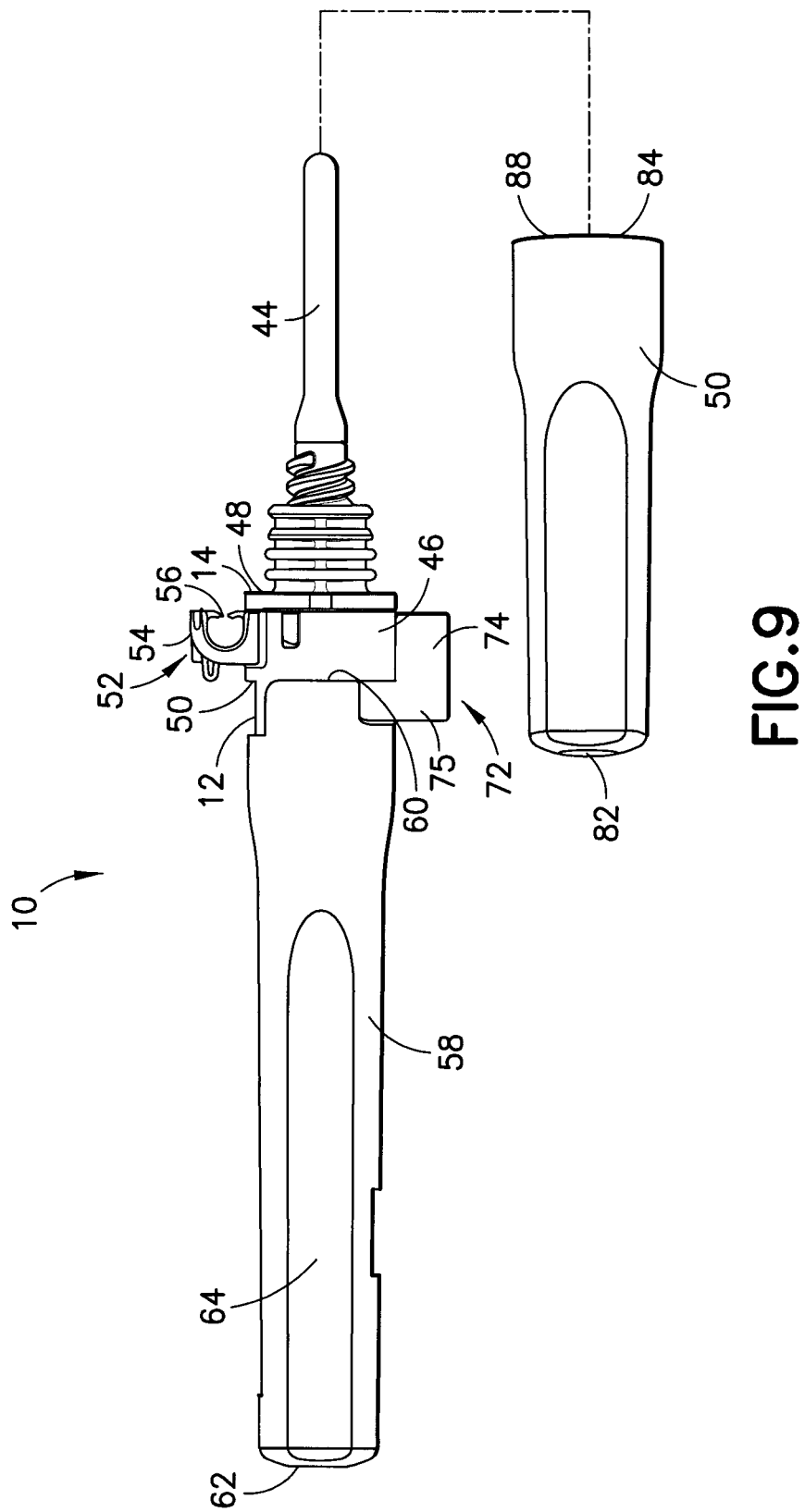
FIG. 9 is a front view of the needle assembly of FIG. 1 showing the assembly with a non-patient shield removed in accordance with an embodiment of the present invention.
Figure 10:
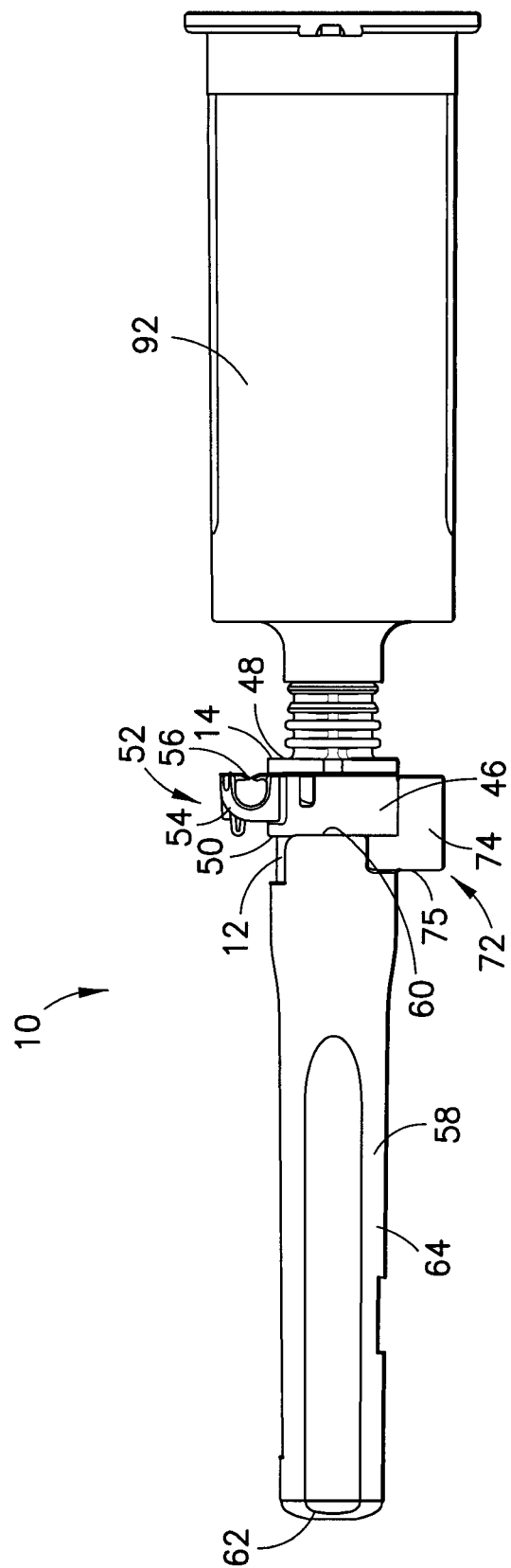
FIG. 10 is a front view of the needle assembly of FIG. 1 showing the assembly with a needle holder secured thereto in accordance with an embodiment of the present invention.
Figure 11:
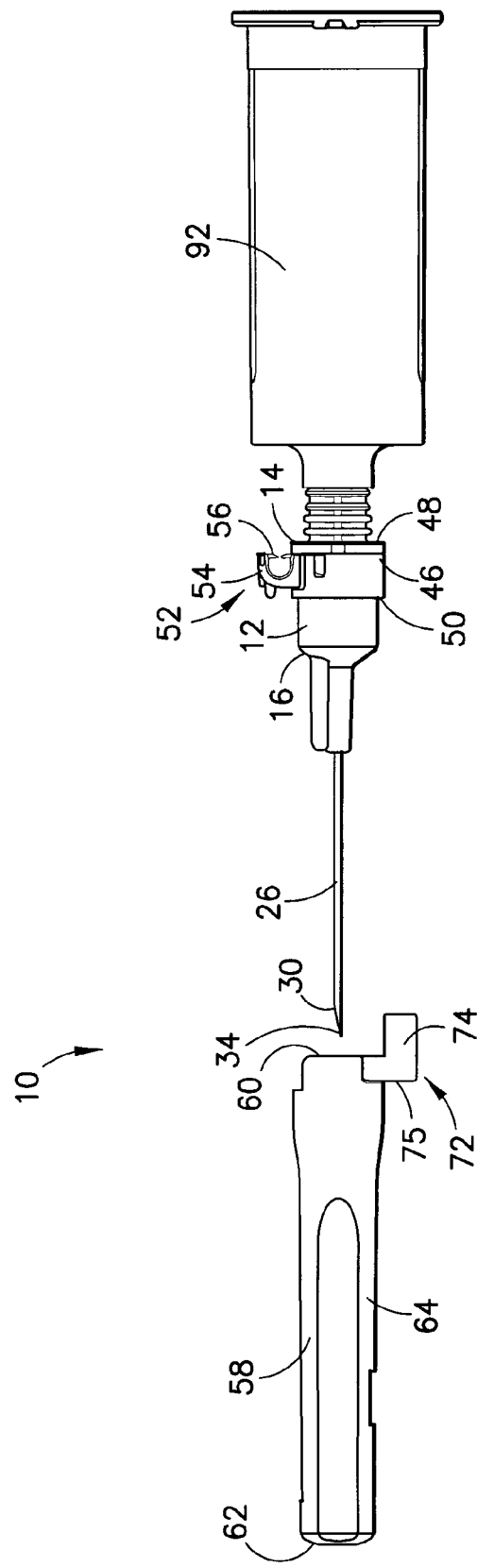
FIG. 11 is a front view of the needle assembly of FIG. 1 showing the assembly with a needle holder secured thereto and the removal of a needle shield in accordance with an embodiment of the present invention.
Figure 12:
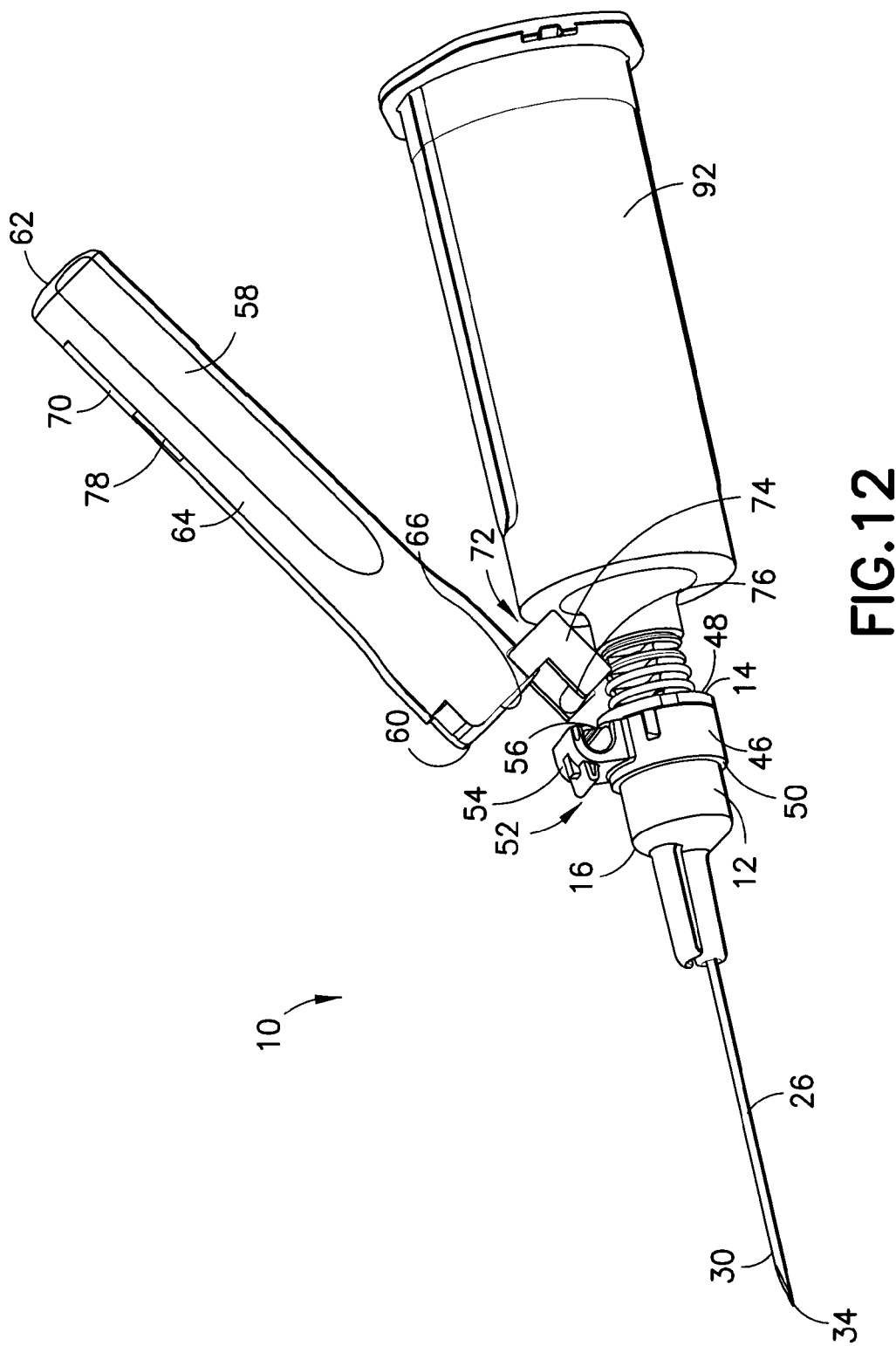
FIG. 12 is a front perspective view of the needle assembly of FIG. 1 showing the attachment of the needle shield in accordance with an embodiment of the present invention.
Figure 13:
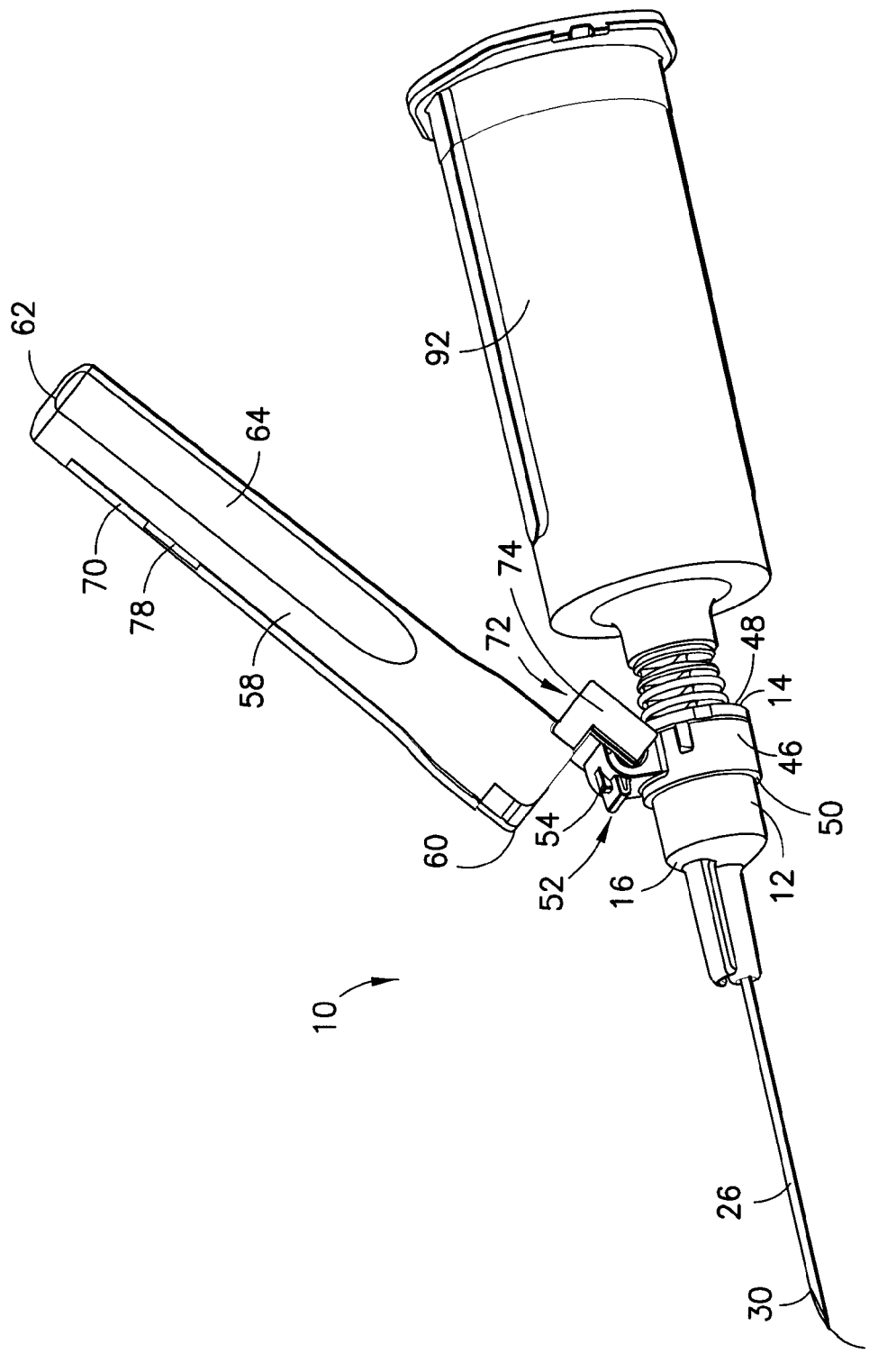
FIG. 13 is a front perspective view of the needle assembly of FIG. 1 showing the needle shield in a non-shielded position in accordance with an embodiment of the present invention.
Figure 14:
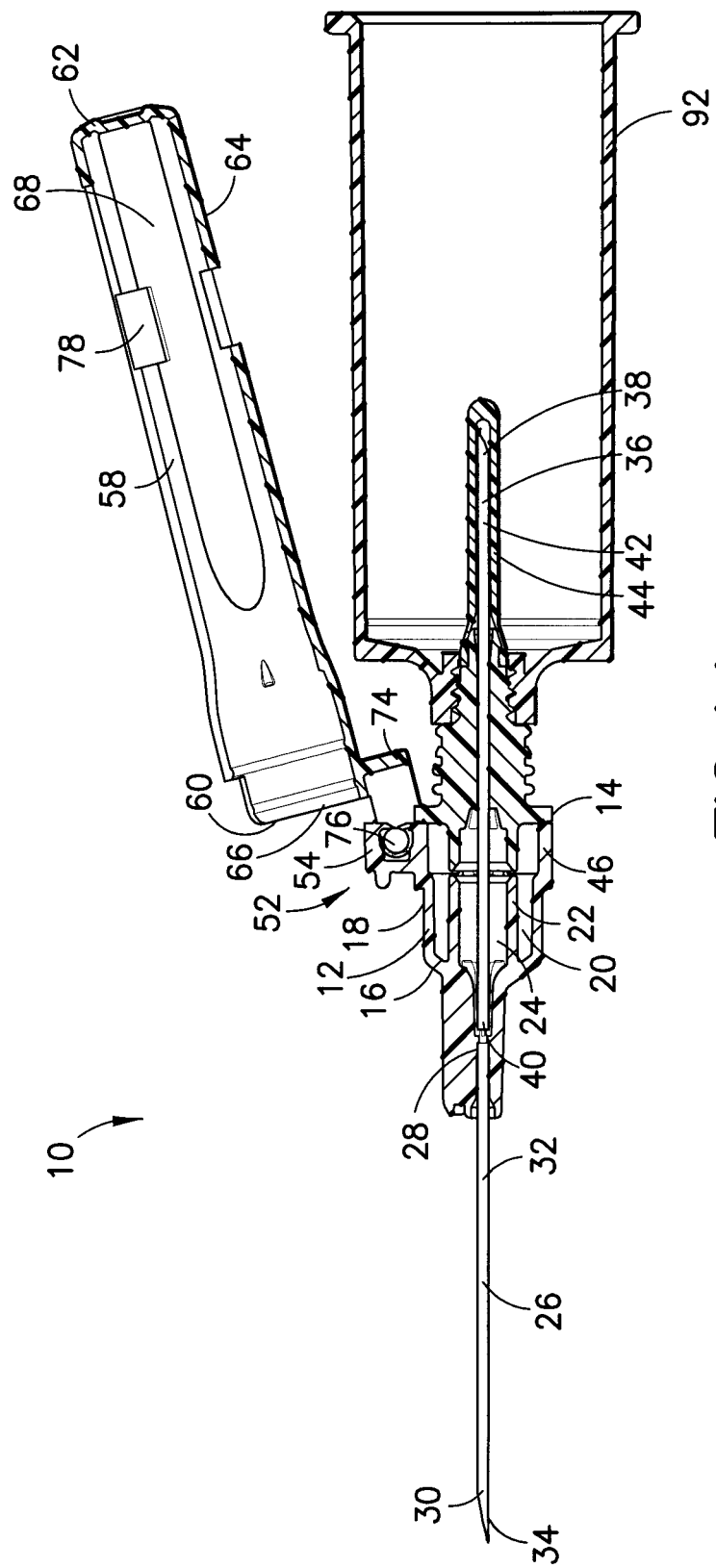
FIG. 14 is a cross-sectional view of the needle assembly shown in FIG. 1 showing the needle shield in a non-shielded position in accordance with an embodiment of the present invention.

Referring to FIGS. 9-18, the IV shield 58 has a pre-use position (shown in FIGS. 9 and 10) and a use position (shown in FIGS. 13-18). When the IV shield 58 is in the pre-use position, the IV shield 58 covers the distal tip 34 of the IV cannula 26. More specifically, in the pre-use position, the interior space 68 of the IV shield 58 receives the IV cannula 26 and the proximal end 60 of the IV shield 58 frictionally engages the housing 12 and abuts the collar 46 of the housing 12. Further, in the pre-use position, the engagement 72 of the IV shield 58 is disengaged from the shield seat 52 and circumferentially spaced from the shield seat 52 on the housing 12. As shown in FIG. 9, for example, the engagement 72 of the IV shield 58 is positioned opposite or 180 degrees from the shield seat 52. As shown in FIG. 11, the IV shield 58 is transitioned from the pre-use position to the use position by moving the IV shield 58 in a distal direction away from the housing 12 to remove the frictional engagement with the housing 12. As shown in FIG. 12, the IV shield 58 is rotated and the engagement 72 of the IV shield 58 is secured to the shield seat 52 of the housing 12 such that the pin 76 is circumferentially surrounded by the C-shaped projection 54. The tapered opening 56 of the C-shaped projection 54 allows the pin 76 to be pushed through the tapered opening 56, but substantially restricts subsequent removal of the pin 76 from the tapered opening 56.

Figure 15:
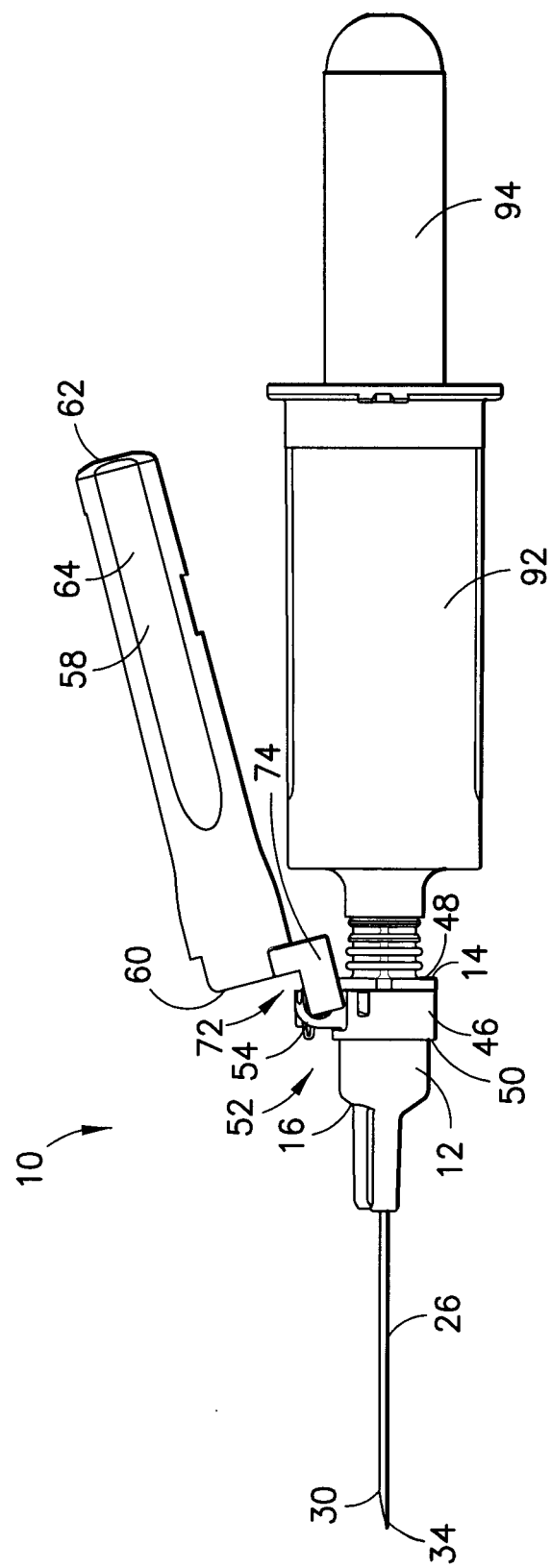
FIG. 15 is a front view of the needle assembly of FIG. 1 showing the needle shield in a non-shielded position and with an evacuated tube received by the needle holder in accordance with an embodiment of the present invention.
Figure 16:
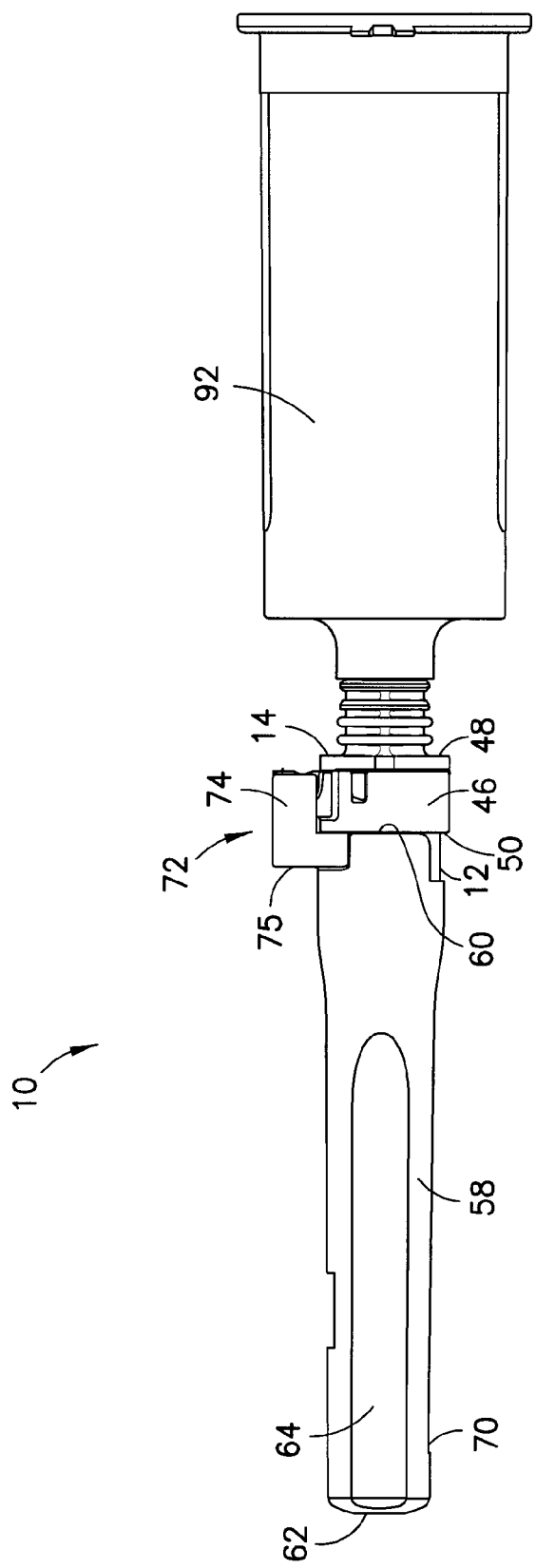
FIG. 16 is a front view of the needle assembly of FIG. 1 showing the needle shield in a shielded position in accordance with an embodiment of the present invention.
Figure 17:
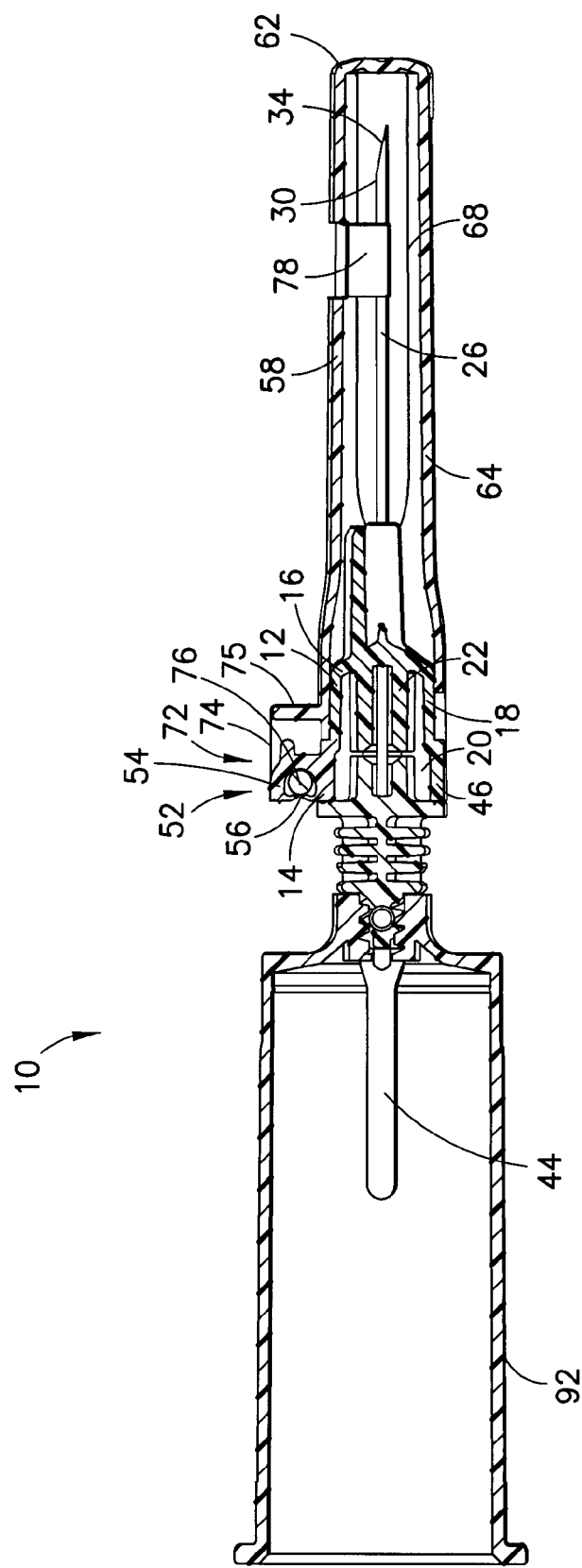
FIG. 17 is a cross-sectional view of the needle assembly shown in FIG. 1 showing the needle shield in a shielded position in accordance with an embodiment of the present invention.
Figure 18:
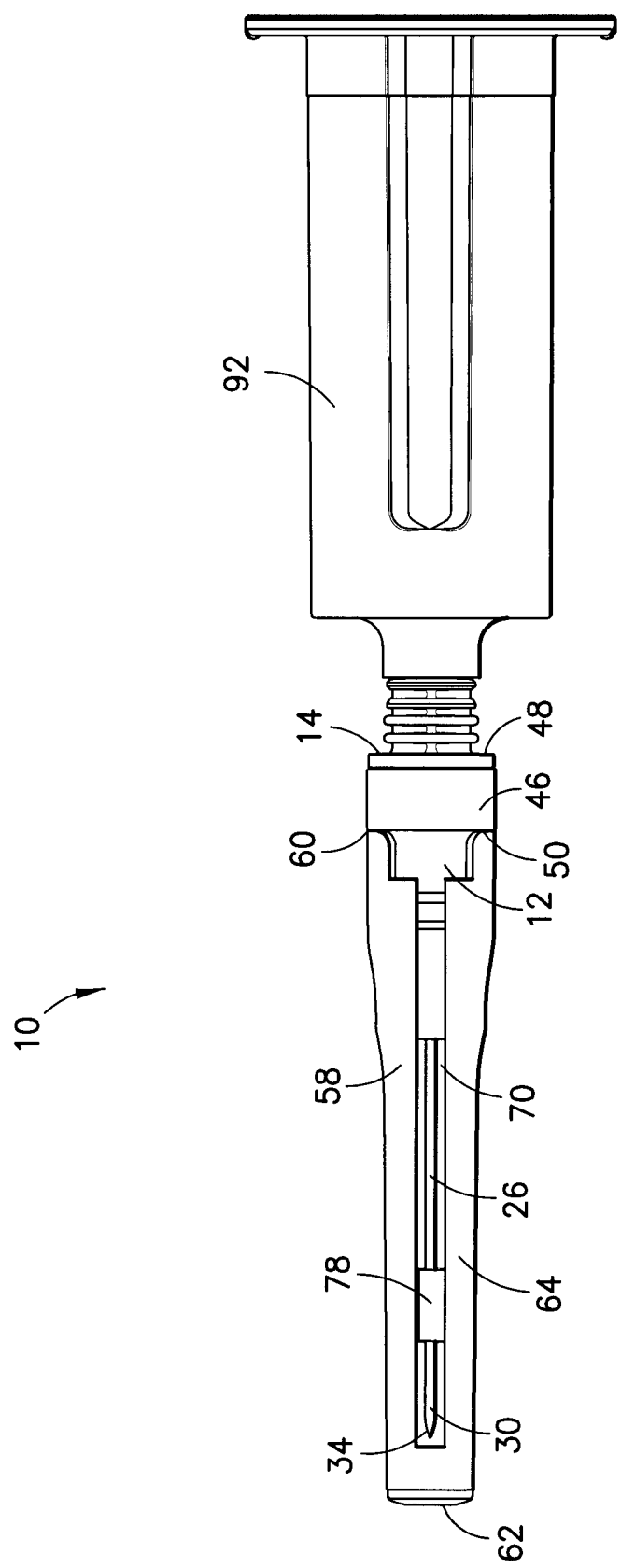
FIG. 18 is a bottom view of the needle assembly of FIG. 1 showing the needle shield in a shielded position in accordance with an embodiment of the present invention.

When in the use position, the IV shield 58 has a non-shielded position (shown in FIGS. 12-15) and a shielded position (shown in FIGS. 16-18). In particular, the IV shield 58 is pivotable between the non-shielded position and the shielded position via the connection between the engagement 72 and the shield seat 52. In the non-shielded position, the IV shield 58 is spaced from the IV cannula 26 and is aligned to the IV cannula 26 at an obtuse angle of, for example, about 120 degrees such that the IV shield 58 does not interfere with the IV cannula 26 during use by a health care technician. The IV shield 58 is transitioned to the shielded position by rotating the IV shield 58 towards the IV cannula 26 such that the longitudinal slot 70 of the elongate body 64 accommodates the IV cannula 26 and allows the IV shield 58 to cover the distal tip 34 of the IV cannula 26. When the IV shield 58 is in the shielded position, the IV cannula 26 is positioned in the interior space 68 of the IV shield 58 with the needle catch 78 engaging the IV cannula 26. The needle catch 78 limits further rotation of the IV shield 58 relative to the housing 12 and IV cannula 26 to prevent exposure of the distal tip 34 after use. The needle catch 78 is a resiliently deflectable member that will yield in response to contact with the IV cannula 26 as the IV shield 58 is rotated toward the IV cannula 26, but returns to an undeflected position and locks the IV cannula 26 within the shield 58.

Referring to FIGS. 9-11, the needle assembly 10 is used by separating the non-patient shield 80 from the collar 46 and threading a needle holder 92 onto the housing 12. Referring to FIGS. 11 and 12, the IV shield 58 is then removed from the housing 12 and secured to the shield seat 52 of the housing 12 as discussed above. With the IV shield 58 in the non-shielded position and rotated away from the IV cannula 26, a phlebotomist guides the distal tip 34 of the IV cannula 26 into a targeted blood vessel (not shown). A pressure differential between the blood in the vein and the pressure within the housing 12 will cause blood to flow through the lumen 32 of the IV cannula 26. Blood will typically appear in the flashback chamber 24 quickly after access to the blood vessel has been attained. Referring to FIG. 15, the phlebotomist then inserts an evacuated tube 94 into the needle holder 92. The evacuated tube 94 includes a rubber stopper that collapses the sleeve 44. The proximal end 38 of the non-patient cannula 36 pierces the sleeve 44 and then pierces the stopper of the evacuated tube 94. The phlebotomist may accumulate one or more samples of blood in this manner.

After collecting the last sample of blood, the phlebotomist urges the needle assembly 10 and needle holder 92 from the patient and rotates the IV shield 58 from the non-shielded position to the shielded position. As a result, the IV cannula 26 is positioned within the interior space 68 of the IV shield 58 with the IV shield 58 surrounding the IV cannula 26. Sufficient rotation of the IV shield 58 causes the needle catch 78 to engage the IV cannula 26 and lock the IV shield 58 to the IV cannula 26. The needle assembly 10 can then be disposed of in a suitable sharps receptacle.

Figure 19:
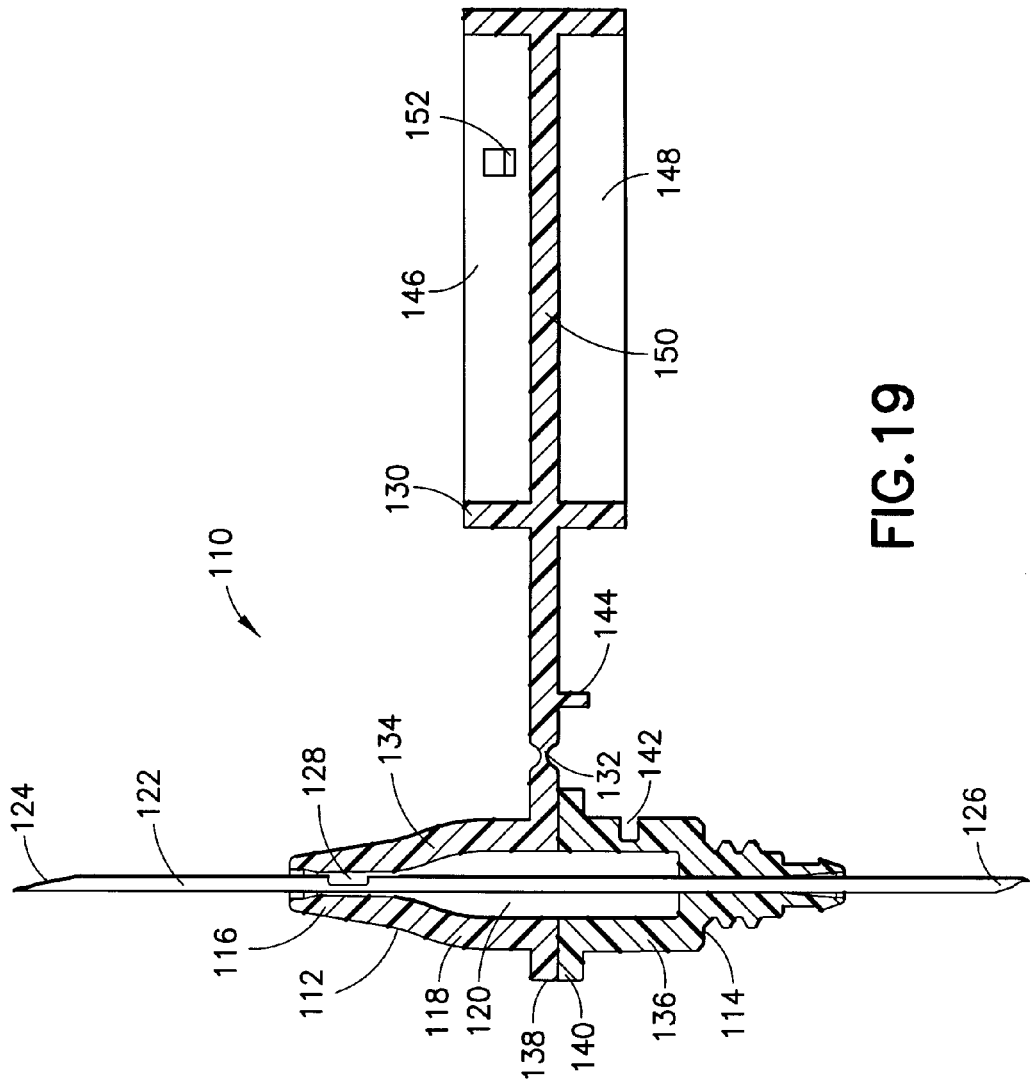
FIG. 19 is a cross-sectional view of a needle assembly according to an embodiment of the present invention.

Referring to FIG. 19, a second embodiment of a needle assembly 110 includes a housing 112 having a proximal end 114 and a distal end 116 with a generally cylindrical-shaped outer sidewall 118 extending between the ends to define a chamber 120 within the housing 112. The needle assembly 110 further includes a cannula 122 extending through the housing 112 and having an IV end 124 projecting distally from the housing 112 and a non-patient end 126 projecting proximally from the housing 112. The cannula 122 defines a notch 128 that is in fluid communication with the chamber 120 of the housing 112. The needle assembly 110 also includes a shield 130 secured to the housing 112 via a living hinge 132, although other suitable arrangements for securing the shield 130 to the housing 112 may be utilized. The housing 112 includes a first portion 134 and a second portion 136 with the first portion 134 secured to the second portion 136 at respective flanges 138, 140 of the first and second portions 134, 136. The first portion 134 and the shield 130 are formed integrally as a single component. The second portion 136 of the housing 112 defines a recess 142 for receiving a catch 144 provided on the shield 130.

Referring still to FIG. 19, the shield 130 includes an IV portion 146 adapted to surround a portion of the IV end 124 of the cannula 122 and a non-patient portion 148 adapted to surround a portion of the non-patient end 126 of the cannula 122. The IV portion 146 and the non-patient portion 148 of the housing are positioned opposite from each other and separated via a central wall 150. The IV portion 146 of the shield 130 includes a needle catch 152 adapted to engage the IV end 124 of the cannula 122. The shield 130 has a pre-use position where the non-patient portion 148 of the shield 130 covers a portion of the non-patient end 126 of the cannula 122 and a use position where the IV portion 146 of the shield 130 covers a portion of the IV end 124 of the cannula 122. The shield 130 is pivotable relative to the housing 112 between the non-patient position and the IV position via the living hinge 132. When the shield 130 is in the pre-use position, the catch 144 on the shield 130 frictionally engages the recess 142 provided on the second portion 136 of the housing 112 to temporarily secure the shield 130 to the housing 112. During use of the needle assembly 110, the shield 130 is pivoted away from the housing 112 to the use position shown in FIG. 19 where the shield 130 is capable of covering the IV end 124 of the cannula 122. A holder (not shown) may then be secured to the second portion 136 of the housing 112 in a similar manner as described above and shown in FIGS. 1-18. After completing a blood sample collection, the shield 130 is pivoted forward towards the housing 112 to cover the IV end 124 of the cannula 122. Upon sufficient movement and/or force, the needle catch 152 engages the cannula 122 and prevents further movement of the shield 130 relative to the housing 112 such that re-exposure of the IV end 124 of the cannula 122 is prevented. Thus, the shield 130 is utilized to shield and protect the non-patient end 126 of the cannula 122 prior to use and also as a safety shield to shield the IV end 124 of the cannula 122 after use.

Referring to FIGS. 20-22, a third embodiment of a needle assembly 170 includes a housing 172 having a proximal end 174 and a distal end 176 with a generally cylindrical-shaped outer sidewall 178 extending between the ends 174, 176 to define a chamber 180 within the housing 172. The needle assembly 170 also includes a cannula 182 extending through the housing 172 and having an IV end 184 projecting distally from the housing 172 and a non-patient end 186 projecting proximally from the housing 172. The cannula 182 defines a notch 188 that is in fluid communication with the chamber 180 of the housing 172. The needle assembly 170 further includes a shield 190 having a body 192 with a first end 194 and a second end 196. The body 192 of the shield 190 includes an IV portion 198 adapted to surround a portion of the IV end 184 of the cannula 182 and a non-patient portion 200 adapted to surround a portion of the non-patient end 186 of the cannula 182. The IV portion 198 and the non-patient portion 200 of the housing 172 are positioned opposite from each other and may be separated via a central wall (not shown) in a similar manner as shown in FIG. 19 and described above. The housing 172 includes a shield seat 202 for securing the shield 190 to the housing 172. The shield seat 202 includes a pair of protrusions 204 extending radially outward from the housing 172 and positioned opposite each other. The shield 190 further includes a mounting portion 206 for engaging the shield seat 202 on the housing 172 to secure the shield 190 to the housing 172. The mounting portion 206 of the shield 190 is formed by one or more inwardly extending projections 208. The shield 190 also includes a needle catch 210 adapted to engage the IV end 184 of the cannula 182.

Referring still to FIGS. 20-22, the shield 190 has a pre-use position where the non-patient portion 200 of the shield 190 covers a portion of the non-patient end 186 of the cannula 182 and a use position where the IV portion 198 of the shield covers a portion of the IV end 184 of the cannula 182. The shield 190 is pivotable relative to the housing 172 between the pre-use position and the use position via the connection between the mounting portion 206 of the shield 190 and the shield seat 202 on the housing 172. In particular, the connection between the shield 190 and the housing 172 allows the shield 190 to rotate 360 degrees. The needle assembly 170 is used in a similar manner as the needle assembly 110 described above and shown in FIG. 11.

Figure 25:
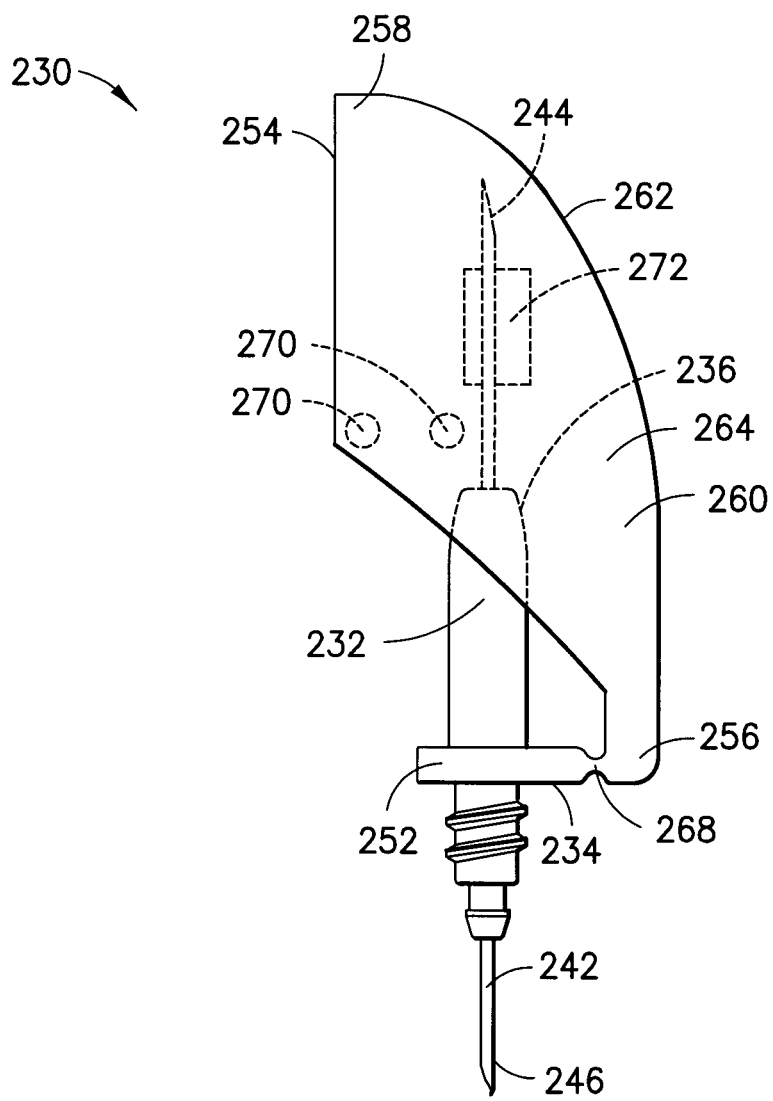
FIG. 25 is a front view of the needle assembly of FIG. 23 showing the shield in a use position and in a shielded position in accordance with an embodiment of the present invention.

Referring to FIGS. 23-25, a fourth embodiment of a needle assembly 230 includes a housing 232 with a proximal end 234, a distal end 236, and a generally cylindrical-shaped outer sidewall 238 extending between the ends 234, 236. Outer sidewall 238 defines a chamber 240 within the housing 232 between the proximal and distal ends 234, 236. The needle assembly 230 further includes a cannula 242 having an IV end 244 projecting distally from the housing 232 and a non-patient end 246 projecting proximally from the housing 232. The cannula 242 defines a notch 248 that is in fluid communication with the chamber 240 of the housing 232. As shown in FIG. 24, a sleeve 250 is mounted over a portion of the non-patient end 246 of the cannula 242. The housing 232 further includes a collar 252 that extends circumferentially around the housing 232. The collar 252 is formed integrally with the housing 232, but also may be formed separately and mechanically secured to the housing 232.

Referring still to FIGS. 23-25, the needle assembly 230 further includes an IV shield 254 with a first end 256 and a second end 258. The IV shield 254 includes an elongate body 260 having an end wall 262 and a pair of sidewalls 264 extending from the end wall 262 to define an interior space 266 for receiving the TV end 244 of the cannula 242. The IV shield 254 is secured to the housing 232 via a living hinge 268. In particular, the first end 256 of the IV shield 254 is secured to the collar 252 of the housing 232. One or both of the sidewalls 264 of the IV shield 254 includes a pair of semi-spherical shaped projections 270 that are adapted to temporarily engage the housing 232. The IV shield 254 also includes a needle catch 272 adapted to engage the IV end 244 of the cannula 242. As shown in FIG. 24, the needle assembly 230 also includes a non-patient shield 274 with a proximal end 276 and a distal end 278. The non-patient shield 274 includes a cylindrical shaped body 280 that defines a pair of openings 282 adjacent to the respective proximal and distal ends 276, 278 of the non-patient shield 274.

The IV shield 254 has a pre-use position (shown in FIG. 23) and a use position (shown in FIGS. 24 and 25). When the IV shield 254 is in the pre-use position, the IV shield 254 covers the IV end 244 of the cannula 242. More specifically, in the pre-use position, the interior space 266 of the IV shield 254 receives the IV end 244 of the cannula 242 and the distal end 236 of the housing is positioned between the semi-spherical shaped projections 270 of the IV shield 254. The IV shield 254 is temporarily held in the pre-use position via the semi-spherical shaped projections 270 of the IV shield 254. The IV shield 254 is transitioned from the pre-use position to the use position by moving the IV shield 254 in a proximal direction away from the housing 232. Upon application of sufficient force to the IV shield 254, the semi-spherical shaped projections 270 will disengage from the housing 232 thereby allowing further rotation of the IV shield 254 to the position shown in FIG. 24.

When in the use position, the IV shield 254 has a non-shielded position (shown in FIG. 24) and a shielded position (shown in FIG. 25). The IV shield 254 is pivotable between the non-shielded position and the shielded position via the living hinge 268. In the non-shielded position, the IV shield 254 is spaced from the IV end 244 of the cannula 242 and is transitioned to the shielded position by rotating the IV shield 254 towards the IV end 244 of the cannula 242 such that the interior space 266 of the IV shield 254 receives the IV end 244 of the cannula 242. As the IV shield 254 is rotated toward the IV end 244 of the cannula 242, the distal end 236 of the housing 232 engages the spherical shaped projections 270 with further rotation of the IV shield 254 causing disengagement of the housing 232 from the spherical shaped projections 270. The IV shield 254 is rotated until the needle catch 272 of the IV shield 254 engages the IV end 244 of the cannula 242, which prevents exposure of the IV end 244 of the cannula 242 after use.

While several embodiments of a fluid sample collection device and method were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:
1. A needle assembly comprising:
a housing having proximal and distal ends and a shield seat;
a cannula projecting distally from the housing, the cannula having a distal tip; and
a single shield having a unitary structure and defining an opening adjacent to a proximal end of the shield and an interior space adapted to receive the cannula;
an engagement extending from the unitary structure of the shield, the single shield configured for transitioning between a pre-use position wherein the shield covers the distal tip of the cannula and the engagement is disengaged and circumferentially spaced from the shield seat, and a use position wherein the engagement is engaged with the shield seat and the shield is adapted to move between a non-shielded position, in which the distal tip is exposed, and a shielded position, in which the distal tip is shielded by the shield and wherein during transition from the pre-use position to the use position, the shield is moved in a direction away from the distal end of the housing to unshield the distal tip of the cannula prior to engagement of the shield engagement with the shield seat.
2. The needle assembly of claim 1, wherein the shield comprises a body that defines a longitudinal slot adapted to receive the cannula.
3. A needle assembly comprising:
a housing having proximal and distal ends and a shield seat;

a cannula projecting distally from the housing, the cannula having a distal tip; and a single shield having a unitary structure and defining an opening adjacent to a proximal end of the shield and an interior space adapted to receive the cannula;

an engagement extending from the unitary structure of the shield, the single shield configured for transitioning between a pre-use position wherein the shield covers the distal tip of the cannula and the engagement is disengaged and circumferentially spaced from the shield seat, and a use position wherein the engagement is engaged with the shield seat and the shield is adapted to move between a non-shielded position, in which the distal tip is exposed, and a shielded position, in which the distal tip is shielded by the shield, wherein the shield comprises a body that defines a longitudinal slot adapted to receive the cannula and the shield includes a needle catch adapted to engage the cannula when the shield is in the shielded position.

4. The needle assembly of claim 2, wherein the body of the shield engages the distal end of the housing when the shield is in the pre-use position.

5. The needle assembly of claim 1, wherein the shield is pivotable relative to the housing when the shield is in the use position.

6. The needle assembly of claim 5, wherein the engagement comprises a locking pin and the shield is pivotable about the locking pin in the use position.

7. A needle assembly comprising:
a housing having proximal and distal ends and a shield seat;
a cannula projecting distally from the housing, the cannula having a distal tip; and
a single shield having a unitary structure and defining an opening adjacent to a proximal end of the shield and an interior space adapted to receive the cannula;
an engagement extending from the unitary structure of the single shield, the shield configured for transitioning between a pre-use position wherein the shield covers the distal tip of the cannula and the engagement is disengaged and circumferentially spaced from the shield seat, and a use position wherein the engagement is engaged with the shield seat and the shield is adapted to move between a non-shielded position, in which the distal tip is exposed, and a shielded position, in which the distal tip is shielded by the shield;
a non-patient cannula projecting from the housing; and
a non-patient shield for removably shielding the non-patient cannula, adapted to engage the proximal end of the housing.

8. The needle assembly of claim 1, wherein the shield seat comprises a projection that defines an opening to receive the engagement of the shield.

9. The needle assembly of claim 8, wherein the opening of the shield seat is tapered to lock the engagement to the shield seat after insertion of the engagement into the opening.

10. The needle assembly of claim 1, wherein the engagement comprises a locking pin, and wherein the shield seat is substantially c-shaped about the locking pin.

11. A needle assembly comprising:
a housing having proximal and distal ends and a shield seat;

a cannula having an IV end projecting distally from the housing and a non-patient end projecting proximally from the housing; and a single shield secured to the housing, said shield having a unitary structure including an IV portion and a non-patient portion opposite from each other and a central wall wherein the IV portion and non-patient portion are separated by the central wall, wherein the shield is configured to transition from a pre-use position wherein the non-patient portion of the shield covers the non-patient end of the cannula, and a use position wherein the IV portion of the shield is capable of covering the IV end of the cannula.

12. The needle assembly of claim 11, wherein the housing comprises a chamber wall extending between the proximal and distal ends for defining a chamber in the housing.

13. The needle assembly of claim 12, wherein the cannula defines an opening in fluid communication with the chamber.

14. The needle assembly of claim 12, wherein the housing comprises a first portion and a second portion with the first portion secured to the second portion, and wherein the shield and the first portion of the housing are formed integrally.

15. The needle assembly of claim 14, wherein the shield is secured to the first portion of the housing via a living hinge, and wherein the shield is pivotable between a non-shielded position and a shielded position.

16. The needle assembly of claim 15, wherein the shield comprises a non-patient portion adapted to cover a portion of the non-patient end of the cannula and an IV portion adapted to cover a portion of the IV end of the cannula.

17. The needle assembly of claim 16, wherein the IV portion of the shield includes a needle catch adapted to engage the IV end of the cannula when the shield is in the use position.

18. The needle assembly of claim 11, wherein the shield comprises a non-patient portion adapted to cover a portion of the non-patient end of the cannula, and an IV portion adapted to cover a portion of the IV end of the cannula, and wherein the IV portion of the shield includes a needle catch adapted to engage the IV end of the cannula when the shield is in the use position.

19. The needle assembly of claim 11, wherein the housing includes a projection, wherein the shield is secured to the housing about the projection with the shield being pivotable relative to the housing between the pre-use position and the use position.

20. The needle assembly of claim 11, wherein the cannula comprises two distinct cannulae.

21. The needle assembly of claim 11, wherein the shield is engaged with the shield seat in the use position and is capable of rotating from a non-shielded position, in which a tip of the IV end is exposed, to a shielded position, in which the tip of the IV end is shielded.

22. The needle assembly of claim 3, wherein during a transition from the pre-use position to the use position, the shield is moved in a distal direction away from the housing to remove the shield from the distal tip of the cannula prior to engagement of the shield engagement with the shield seat.

23. The needle assembly of claim 7, wherein during a transition from the pre-use position to the use position, the shield is moved in a distal direction away from the housing to remove the shield from the distal tip of the cannula prior to engagement of the shield engagement with the shield seat.

* * * * *

UNITED STATES PATENT AND TRADEMARK OFFICE
CERTIFICATE OF CORRECTION

PATENT NO.         : 9,572,929 B2                                      Page 1 of 1
APPLICATION NO.    : 13/788277
DATED              : February 21, 2017
INVENTOR(S)        : Lee Hoong Sim et al.

It is certified that error appears in the above-identified patent and that said Letters Patent is hereby corrected as shown below:

On the Title Page

Column 1, Item (72), Inventors, Line 2, delete "Kukai" and insert -- Kulai --

Signed and Sealed this
Eighteenth Day of April, 2017

Michelle K. Lee
*Director of the United States Patent and Trademark Office*